US012635880B2

(12) United States Patent
Chang et al.

(10) Patent No.: US 12,635,880 B2
(45) Date of Patent: May 26, 2026

(54) OPTICAL DETECTION SYSTEM CAPABLE OF PROVIDING AUXILIARY LIGHT SOURCE PROJECTION

(71) Applicant: Crystalvue Medical Corporation, Taoyuan City (TW)

(72) Inventors: Yen-Jen Chang, Taoyuan City (TW); William Wang, Taoyuan City (TW); Che-Liang Tsai, Taoyuan City (TW)

(73) Assignee: Crystalvue Medical Corporation, Taoyuan City (TW)

( * ) Notice: Subject to any disclaimer, the term of this patent is extended or adjusted under 35 U.S.C. 154(b) by 458 days.

(21) Appl. No.: 18/195,266

(22) Filed: May 9, 2023

(65) Prior Publication Data

US 2023/0404403 A1 Dec. 21, 2023

(30) Foreign Application Priority Data

May 24, 2022 (TW) .................................. 111119348

(51) Int. Cl.
A61B 3/15 (2006.01)
A61B 3/00 (2006.01)

(52) U.S. Cl.
CPC ............ A61B 3/154 (2013.01); A61B 3/0008 (2013.01); A61B 3/152 (2013.01)

(58) Field of Classification Search
CPC ........ A61B 3/154; A61B 3/0008; A61B 3/152
USPC ........................................ 351/208
See application file for complete search history.

(56) References Cited

U.S. PATENT DOCUMENTS

| 7,513,619 B2 * | 4/2009 | Lacombe | A61B 3/102 |
| | | | 356/497 |
| 2006/0119794 A1 * | 6/2006 | Hillis | G02B 3/14 |
| | | | 351/205 |
| 2008/0002151 A1 * | 1/2008 | Hideshima | A61B 3/102 |
| | | | 351/208 |
| 2009/0310083 A1 * | 12/2009 | Campbell | A61B 3/1225 |
| | | | 351/215 |

(Continued)

FOREIGN PATENT DOCUMENTS

| CN | 112244757 A * | 1/2021 | ............ A61B 3/117 |
| WO | WO-2008037090 A1 * | 4/2008 | ........... A61B 3/0008 |

OTHER PUBLICATIONS

CN-112244757-A—Li—English translation—Jan. 2021.*

(Continued)

*Primary Examiner* — Sharrief I Broome
(74) *Attorney, Agent, or Firm* — Patterson + Sheridan, LLP

(57) ABSTRACT

An optical detection system capable of providing auxiliary light source projection including an optical detection apparatus and an optical module is disclosed. The optical module and the optical detection apparatus are combined with each other in a specific combination type. The specific combination type can be a direct integration type, a bending type, a foldable type, a low height type or an attachable type. The optical module is used to provide additional auxiliary light source projection to improve a condition for testee to gaze and observe a pattern. The optical module includes a light source, a lens set and a reflecting mirror. The light source can be designed as different types of multiple light sources, such as an opposite-direction type multiple light sources or a ring type multiple light sources, to provide a uniform light source.

10 Claims, 8 Drawing Sheets

(56)  References Cited

U.S. PATENT DOCUMENTS

| | | | |
|---|---|---|---|
| 2009/0316111 A1* | 12/2009 | Hunter | A61B 3/10 351/201 |
| 2013/0128223 A1* | 5/2013 | Wood | A61B 3/1208 351/246 |
| 2014/0211161 A1* | 7/2014 | Yam | A61B 3/14 600/398 |
| 2015/0366447 A1* | 12/2015 | Su | A61B 3/0016 351/206 |
| 2016/0038025 A1* | 2/2016 | Irsch | G02B 27/141 351/215 |
| 2017/0325676 A1* | 11/2017 | Lichtenauer | A61B 3/024 |
| 2019/0038766 A1* | 2/2019 | Mohanty | A61K 41/00 |
| 2021/0315451 A1* | 10/2021 | Kurtz | A61B 5/0013 |
| 2022/0257114 A1* | 8/2022 | Schottner | A61B 3/12 |
| 2022/0331042 A1* | 10/2022 | Böhme | A61B 3/135 |

OTHER PUBLICATIONS

Phan, Alex et al. "Design of an Optical Pressure Measurement System for Intraocular Pressure Monitoring." IEEE sensors journal 18.1 (2018): 61-68. Web. (Year: 2018).*

* cited by examiner

Optical detection system ODS

Optical detection system ODS

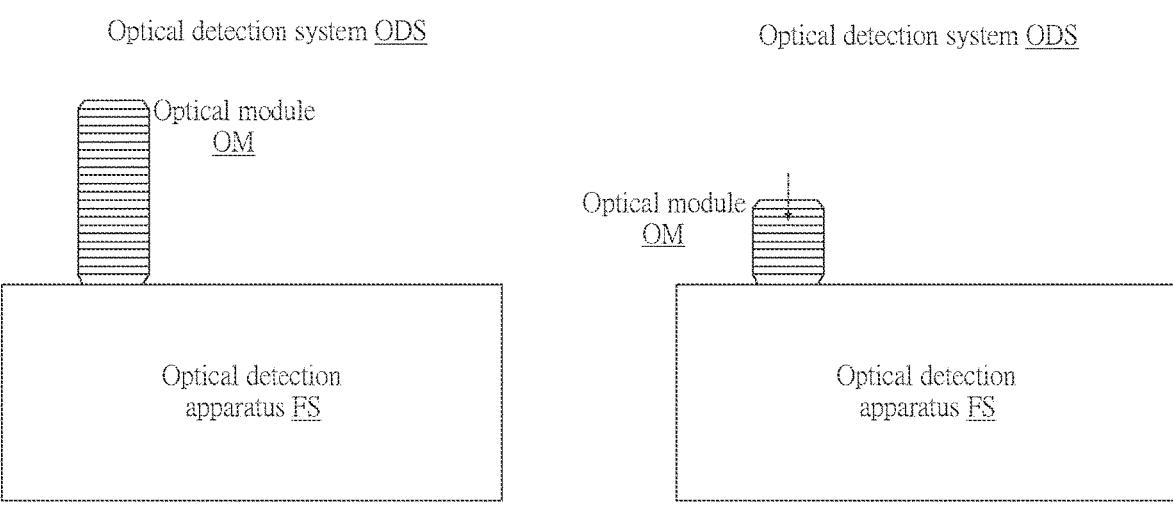
FIG. 5A                        FIG. 5B

Optical detection system ODS

Optical module OM

Connection
portion
CP

Optical detection
apparatus FS

Optical detection system ODS

Optical module OM

Connection
portion
CP

Optical detection
apparatus FS

Reverse type multi-light source
OML

Ring-shaped multi-light source
RML

OPTICAL DETECTION SYSTEM CAPABLE OF PROVIDING AUXILIARY LIGHT SOURCE PROJECTION

BACKGROUND OF THE INVENTION

Related Application

This application claims the benefit of TW Patent Application No. 111119348, filed May 24, 2022, the contents of which are incorporated herein by reference in its entirety.

FIELD OF THE INVENTION

The invention relates to optical device; in particular, to an optical detection system capable of providing auxiliary light source projection.

DESCRIPTION OF THE PRIOR ART

In general, when the conventional optical detection system implements optical detection for the eyes of the testee, the design of patterns or light spots is usually provided to allow the eyes of the testee to observe and gaze. If more than two light sources are configured, light spots at different positions can be turned on for the testee to gaze at, so as to achieve the effect of rotating the testee's eyeballs.

However, the application design of the above-mentioned prior art is to dispose the optical path design of the gazing pattern or light spot in the optical detection apparatus, thus causing it to be combined with other optical design optical paths in the optical detection apparatus, resulting in many additional limitations. Therefore, the above-mentioned problems still need to be solved urgently.

SUMMARY OF THE INVENTION

Therefore, the invention provides an optical detection system for auxiliary light source projection, which can combine the optical path design of the gazing pattern or light spot with the optical module by adding a light source, one or more reflectors and a beam splitter, and can be independent of the optical detection apparatus to solve the above-mentioned problems of the prior arts.

An embodiment of the invention is an optical detection system capable of providing auxiliary light source projection. In this embodiment, the optical detection system includes an optical detection apparatus and an optical module. The optical module and the optical detection apparatus are combined with each other in a specific combination type. The optical module includes a light source, a lens set and a reflecting mirror. The optical module is configured to provide additional auxiliary light source projection to improve the condition for the testee to gaze and observe patterns.

In an embodiment, the specific combination type is a direct integration type, and the optical module is directly integrated with the optical detection apparatus.

In an embodiment, the specific combination type is a bending type, and the optical module is connected to the optical detection apparatus and the optical module is in a bent or upright state.

In an embodiment, the specific combination type is a foldable type, the optical module is connected to the optical detection apparatus and the optical module is in a folded or unfolded state.

In an embodiment, the specific combination type is a low height type, and lights emitted by the light source in the optical module are incident to the lens set through at least one reflection on an inner wall of the optical module.

In an embodiment, the specific combination type is an attachable type, and the optical module can be attached to or detached from the optical detection apparatus.

In an embodiment, the light source is designed as a multi-light source to provide a uniform light source.

In an embodiment, the light source is designed as a reverse type multi-light source.

In an embodiment, the light source is designed as a ring-shaped multi-light source.

In an embodiment, the optical detection apparatus is an optical ophthalmology detection apparatus to perform the optical detection on the testee's eyes.

Compared to the prior art, the optical detection system proposed by the invention can be independent of the optical detection apparatus by adding a light source, one or more reflectors and a beam splitter to combine the optical path design of the gazing pattern or light spot with the optical module. Since it does not need to be combined with other optical design optical paths in the optical detection apparatus, additional restrictions can be greatly reduced to effectively solve the problems encountered in the prior arts.

The advantage and spirit of the invention may be understood by the following detailed descriptions together with the appended drawings.

BRIEF DESCRIPTION OF THE APPENDED DRAWINGS

FIG. 5A and FIG. 5B illustrate schematic diagrams showing the optical module connected to the optical detection apparatus and the optical module can be in a folded or unfolded state respectively.

DETAILED DESCRIPTION OF THE INVENTION

Figure 1:
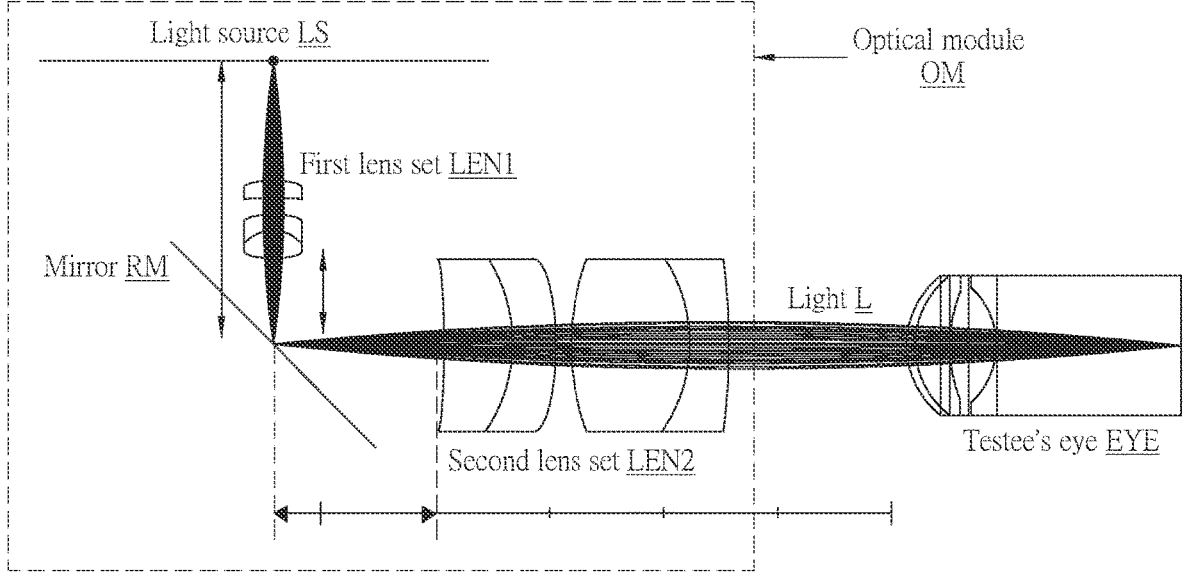
FIG. 1 and FIG. 2 illustrate schematic diagrams of the optical module in the optical detection system capable of providing auxiliary light source projection in the invention.

Exemplary embodiments of the invention are referenced in detail now, and examples of the exemplary embodiments are illustrated in the drawings. Further, the same or similar reference numerals of the components/components in the drawings and the detailed description of the invention are used on behalf of the same or similar parts.

A specific embodiment of the invention is an optical detection system. In fact, the optical detection system can be designed in different types according to the requirements of practical applications, such as a machine type optical detection system or a portable/wearable type optical detection system, without any specific limitations.

In this embodiment, the optical detection system includes an optical detection apparatus and an optical module. The optical module is an accessory module attached to many optical detection apparatuses. The optical detection system can be independent of the optical detection apparatus by adding a light source, one or more reflectors and a beam splitter to combine the optical path design of the gazing pattern or light spot with the optical module, so that the gazing pattern or the optical path design of the light point does not need to be combined with other optical design optical paths in the optical detection apparatus, which can greatly reduce the occurrence of additional restrictions.

Figure 2:
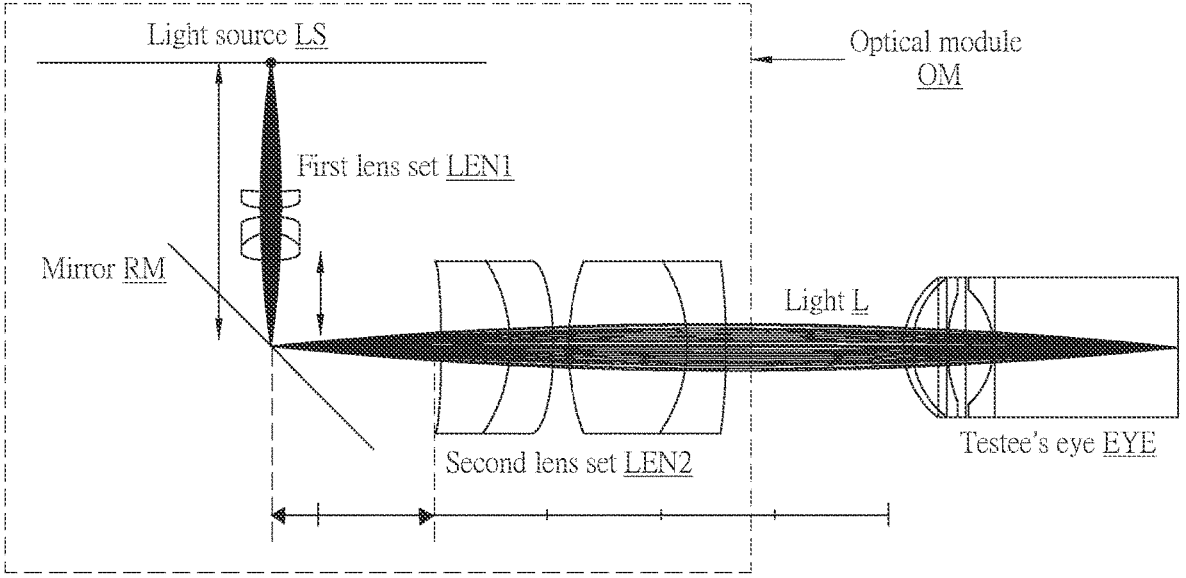

Please refer to FIG. 1 and FIG. 2. FIG. 1 and FIG. 2 illustrate schematic diagrams of the optical module in an optical detection system capable of providing auxiliary light source projection according to the invention. As shown in FIG. 1 and FIG. 2, the optical module OM may include a light source LS, a first lens set LEN1, a second lens set LEN2 and a mirror RM. The light source LS of the optical module OM emits a light L and the light L passes through the first lens set LEN1 and is reflected by the mirror RM, and the reflected light L passes through the second lens set LEN2 to provide a weak light spot that can be directly viewed by the testee to the tester's eyes EYE.

It should be noted that the number of the light source LS, the first lens set LEN1, the second lens set LEN2 and the reflector RM included in the optical module OM and the positions thereof can be adjusted according to actual application requirements, and it is not limited to what is shown in FIG. 1 and FIG. 2.

In this embodiment, the optical detection system ODS includes an optical detection apparatus FS and an optical module OM. The optical detection apparatus FS is an optical ophthalmological detection device, which is used for optical detection of the testee's eyes. The optical module OM is combined with the optical detection apparatus FS in a specific combination type. When the optical detection apparatus FS provides a pattern to allow the testee's eyes to gaze and observe, the optical module OM will provide an additional auxiliary light source projection to improve the condition for the testee's eyes to gaze and observe the pattern.

In practical applications, the specific combination type can be a direct integration type, a bending type, a foldable type, a low height type and an attachable type, but not limited to this.

Figure 3:
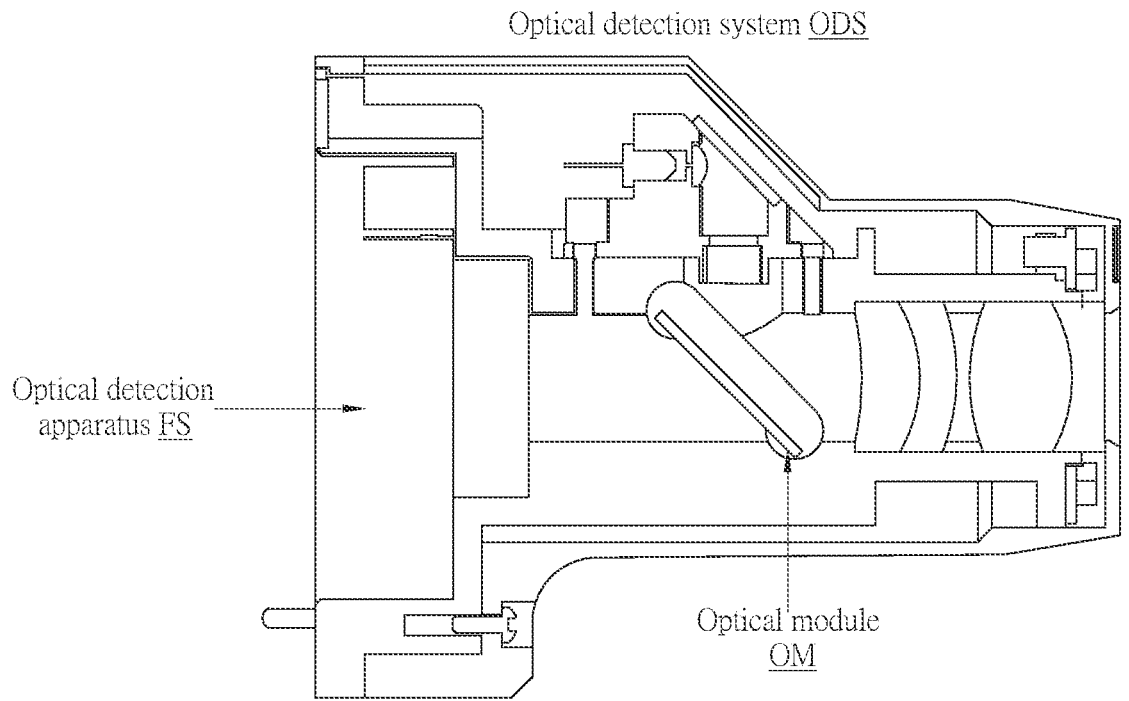
FIG. 3 illustrates a schematic diagram of the direct integration of the optical module and the optical detection apparatus.

As shown in FIG. 3, when the specific combination type is a direct integration type, the optical module OM is directly integrated with the optical detection apparatus FS, but not limited to this.

Figure 4A:
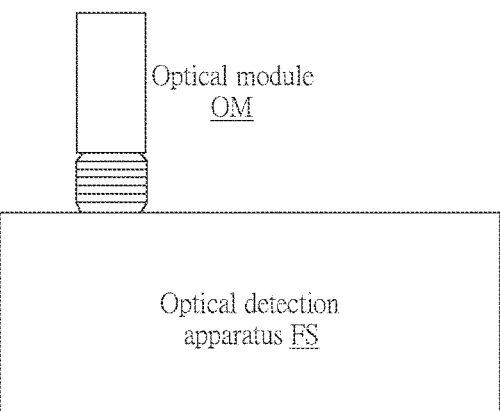
FIG. 4A and FIG. 4B illustrate schematic diagrams showing the optical module connected to the optical detection apparatus and the optical module can be in a bent or upright state respectively.
Figure 4B:
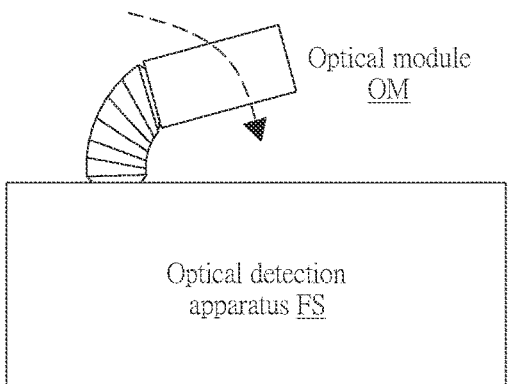

As shown in FIG. 4A and FIG. 4B, when the specific combination type is a bending type, the optical module OM is connected to the optical detection apparatus FS and the optical module OM can be presented as a bent or upright state, but not limited to this.

As shown in FIG. 5A and FIG. 5B, when the specific combination type is a foldable type, the optical module OM is connected to the optical detection apparatus FS and the optical module OM can be presented as a folded or unfolded state, but not limited to this.

Figure 6:
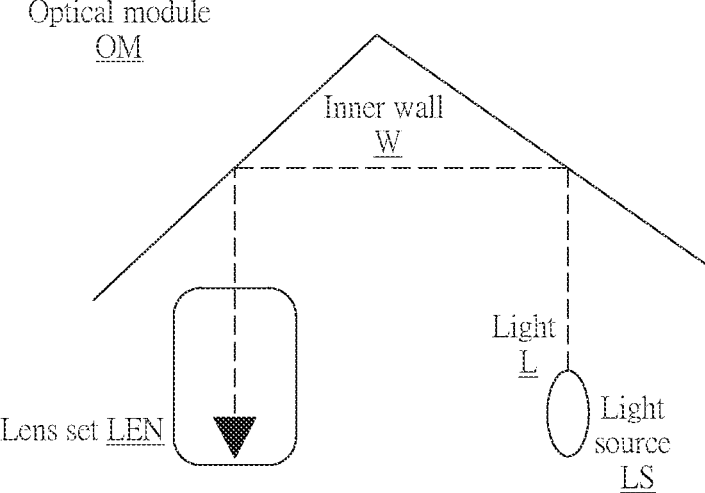
FIG. 6 illustrates a schematic diagram showing that the light emitted by the light source in the optical module passes through at least one reflection on the inner wall of the optical module and hits the lens set.

As shown in FIG. 6, when the specific combination type is a low height type, the light L emitted by the light source LS in the optical module OM passes through at least one of the inner walls W of the optical module OM and then reflected to the lens set LEN, but not limited to this.

Figure 7A:
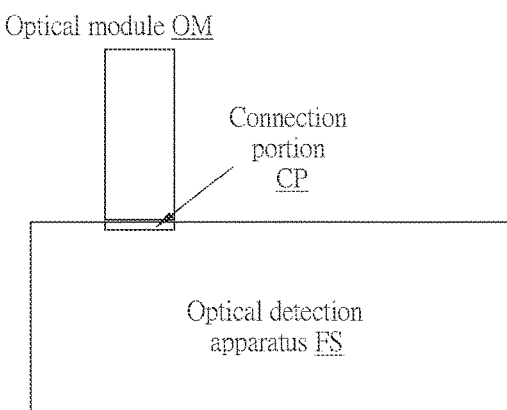
FIG. 7A and FIG. 7B illustrate schematic diagrams showing that the optical module can be attached to or detached from the optical detection apparatus respectively.
Figure 7B:
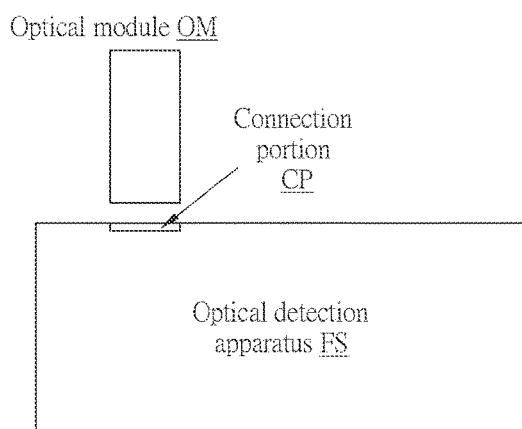

As shown in FIG. 7A and FIG. 7B, when the specific combination type is an attachable type, the optical module OM can be attached to the connection portion CP of the optical detection apparatus FS or separated from the connection portion of the optical detection apparatus FS CP, but not limited to.

Figure 8:
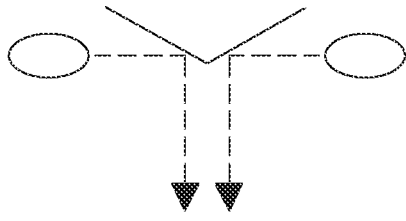
FIG. 8 illustrates a schematic diagram of the light source system designed as a reverse type of multi-light source.
Figure 9:
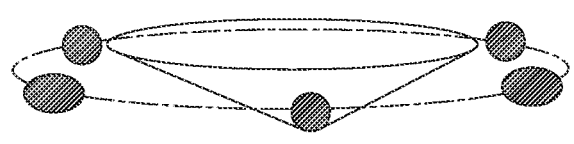
FIG. 9 illustrates a schematic diagram of the light source system designed as a ring-shaped multi-light source.

In practical applications, the light source LS in the optical module OM can be designed as multi-light sources of different types, so as to provide a uniform light source. For example, the light source LS can be designed as a reverse type multi-light source OML as shown in FIG. 8 or a ring-shaped multi-light source RML as shown in FIG. 9, but not limited to this.

Compared to the prior art, the optical detection system proposed by the invention can be independent of the optical detection apparatus by adding a light source, one or more reflectors and a beam splitter to combine the optical path design of the gazing pattern or light spot with the optical module. Since it does not need to be combined with other optical design optical paths in the optical detection apparatus, additional restrictions can be greatly reduced to effectively solve the problems encountered in the prior arts.

With the example and explanations above, the characteristics and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. An optical detection system, comprising:
an optical detection apparatus, configured to perform an optical detection on a testee; and
an optical module, independent of the optical detection apparatus and combined with the optical detection apparatus in a specific combination type, comprising a light source, a first lens set, a second lens set and a reflecting mirror, and the optical module being configured to provide additional auxiliary light source projection to improve a condition for the testee to gaze and observe patterns;
wherein the light source of the optical module lights emits a light and the light passes through the first lens set and is reflected by the reflecting mirror, and the reflected light passes through the second lens set to provide a weak light spot that can be directly viewed by the testee to the testee's eyes.

2. The optical detection system of claim 1, wherein the specific combination type is a direct integration type, and the optical module is directly integrated with the optical detection apparatus.

3. The optical detection system of claim 1, wherein the specific combination type is a bending type, and the optical module is connected to the optical detection apparatus and the optical module is in a bent or upright state.

4. The optical detection system of claim 1, wherein the specific combination type is a foldable type, the optical module is connected to the optical detection apparatus and the optical module is in a folded or unfolded state.

5. The optical detection system of claim 1, wherein the specific combination type is a low height type, and lights emitted by the light source in the optical module are incident to the first lens set through at least one reflection on an inner wall of the optical module.

6. The optical detection system of claim 1, wherein the specific combination type is an attachable type, and the optical module can be attached to or detached from the optical detection apparatus.

7. The optical detection system of claim 1, wherein the light source is designed as a multi-light source to provide a uniform light source.

8. The optical detection system of claim 7, wherein the light source is designed as a reverse type multi-light source.

9. The optical detection system of claim 7, wherein the light source is designed as a ring-shaped multi-light source.

10. The optical detection system of claim 1, wherein the optical detection apparatus is an optical ophthalmology detection apparatus to perform the optical detection on the testee's eyes.

* * * * *